United States Patent [19]

Helbig et al.

[11] Patent Number: 5,143,732
[45] Date of Patent: Sep. 1, 1992

[54] ORALLY ADMINISTERED PHARMACEUTICAL AGENT FOR IRON AND MAGNESIUM SUBSTITUTIVE THERAPY

[75] Inventors: Joachim Helbig, Tutzing; Hans G. Classen, Stuttgart, both of Fed. Rep. of Germany

[73] Assignee: Verla-Pharm Arzneimittelfabrik Apotheker H.J. V. Ehrlich GmbH & Co., Tutzing, Fed. Rep. of Germany

[21] Appl. No.: 323,993

[22] Filed: Mar. 15, 1989

[30] Foreign Application Priority Data

Mar. 22, 1988 [DE] Fed. Rep. of Germany ....... 3809625

[51] Int. Cl.$^5$ ..................... A61K 33/26; A61K 33/14; A61K 31/295; A61K 31/205
[52] U.S. Cl. .................................. 424/647; 424/648; 424/663; 424/665; 514/502; 514/566
[58] Field of Search ............... 424/646, 647, 648, 661, 424/663, 665, 679, 681, 682, 678; 514/502, 566

[56] References Cited

U.S. PATENT DOCUMENTS

4,751,085  6/1988  Gaull .................................. 424/646

OTHER PUBLICATIONS

"The Pharmacological Basis of Therapeutics," Goodman and Gilman, Pergamon Press, New York, N.Y., pp. 1286 and 907 (1990).
"Magnesium Supplementation in Pregnancy," Spatling et al., Brit. J. Obstet. Gyn. 95:120-25 (Feb. 1988).
"Is Milk of Magnesia a Potentially Effective Antidote . . . ", Chadwick and Corby, Vet. Hum. Toxicol. (1982), pp. 187-188.
"Effect of Orally Administered Magnesium Hydroxide . . . ", Corby et al., Clin. Toxicol. 23(768):489-99 (1985-1986).
"Inhibition of Iron Absorption by Magnesium Trisilicate," Hall et al., Med. J. Australia (Jul. 12, 1969), pp. 95-96.
"Magnesium Carbonate," Leming et al., Ann. Int. Med., vol. 94(5):660 (May 1981).
"Effect of a Heal of Iron Absorption . . . ", Seligman et al., Blood 64 (Supp.), p. 42a (1984).

Primary Examiner—Frederick E. Waddell
Assistant Examiner—Raymond J. Henley, III
Attorney, Agent, or Firm—Venable, Baetjer, Howard & Civiletti

[57] ABSTRACT

An orally administered pharmaceutical agent that is particularly suited for iron and magnesium substitutive therapy is disclosed. This drug consists of a combination of one or more pharmaceutically and physiologically compatible iron compounds, one or more pharmaceutically and physiologically compatible magnesium compounds, and, if the magnesium compounds do not contain any chlorine atoms dissociable in aqueous media and saturating the available magnesium valences, the drug further consists of one or more pharmaceutically and physiologically compatible compounds providing chlorine ions in aqueous media. The iron compounds, magnesium compounds and chlorine ion supplying compounds may be mixed with the conventional pharmaceutical solvents and/or thinners and/or auxiliary matter. Unexpectedly, this drug makes it possible to simultaneously administer magnesium or calcium compounds with iron compounds, without thereby causing reduced iron resorption.

18 Claims, 2 Drawing Sheets

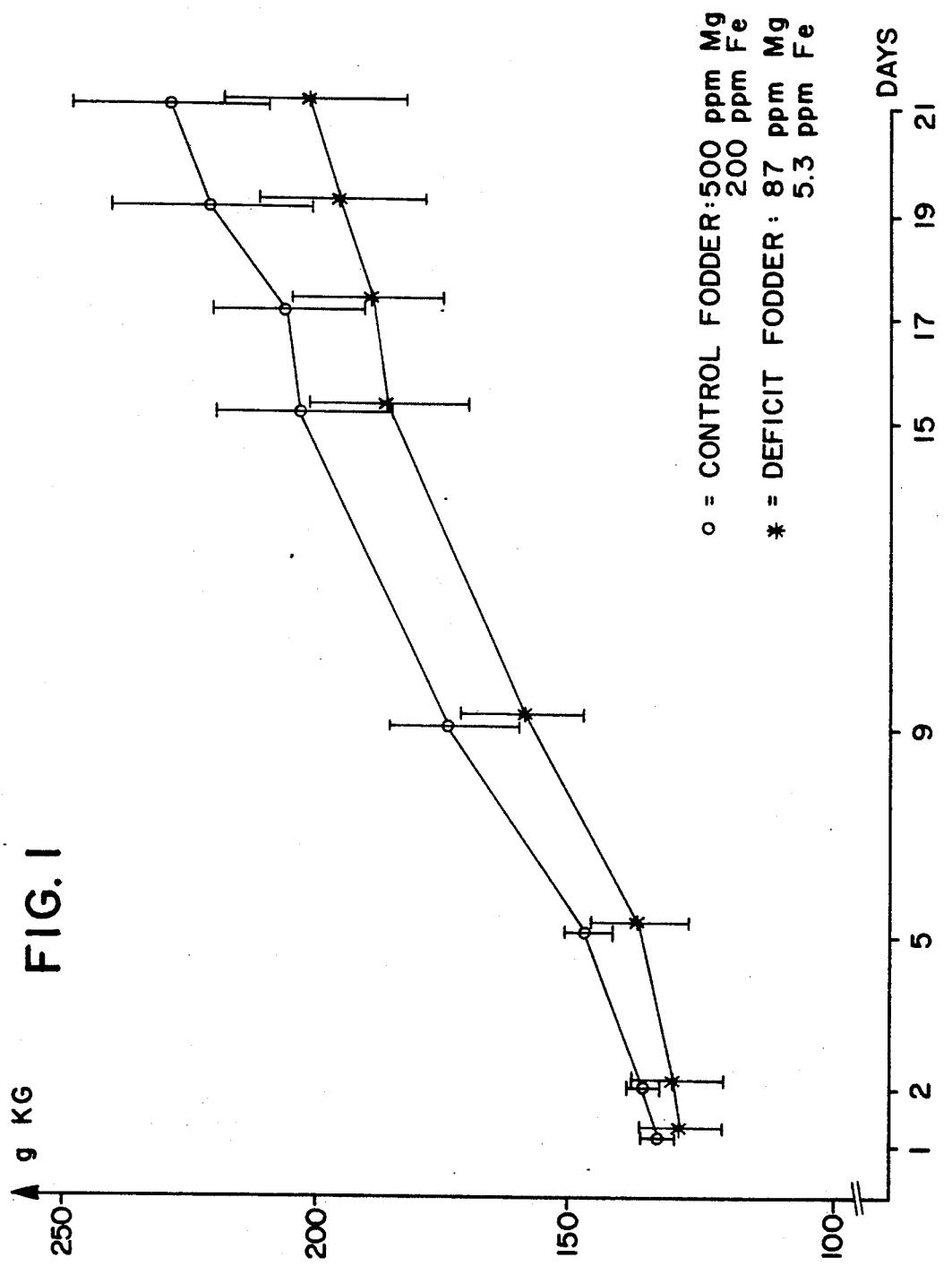

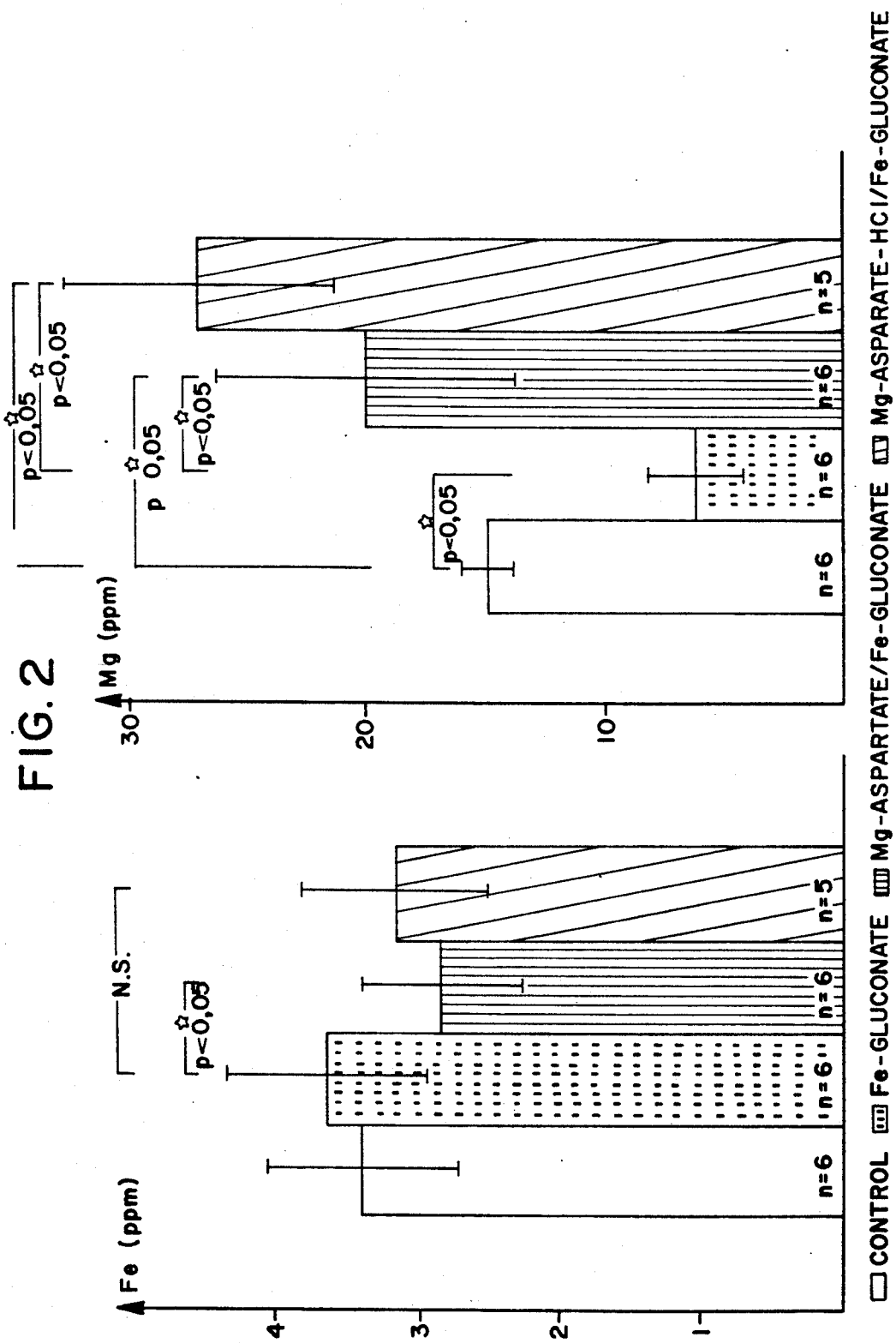

ORALLY ADMINISTERED PHARMACEUTICAL AGENT FOR IRON AND MAGNESIUM SUBSTITUTIVE THERAPY

BACKGROUND OF THE INVENTION

Today's nutrition provides the human organism with too few essential elements such as magnesium, iron and calcium. A deficiency of magnesium and iron is especially critical is pregnant women, who have a higher need for magnesium and iron in order to prevent anemia and poor birth results (Huth et al., "Textbook on Nutritional Therapy," published by Georg Thieme, Stuttgart-New York, pp. 100-101; Koller, "Risk Factors of Pregnancy," published by Springer, Berlin/Heidelberg-/New York/Tokyo 1983, p. 326; Forth et al., "Pharmacology and Toxicology," by the scientific publishers Mannheim/Vienna/Zurich, 5th Edition, pp. 389-392; and "Magnesium: Its Biologic Significance," by J. K. Aikawa, CRC Press, Inc., Boca Raton, Flor., pp. 112-113). Dispensation of magnesium and iron preparations to pregnant women is therefore indicated.

However, it is known that iron resorption is substantially reduced when pharmaceutical magnesium and iron compounds are administered orally simultaneously. This is particularly true if a subacidification of gastric fluid occurs. Therefore, when basic magnesium compounds such as magnesium hydroxide and salts of iron (II) and iron (III) are administered simultaneously, a reduced iron resorption can be registered (Corby et al., *Clinical Toxicology* 23, 489-99 (1985-86)). Additionally, Hall et al., *The Medical Journal of Australia,* pages 95-96 (1969), give a description of suppressed iron resorption during simultaneous administration of magnesium trisilicate.

Previously, it was therefore necessary to administer magnesium and iron preparations separately with several hours' interval between the administration of each agent. Naturally this dosing regimen is inconvenient and reduces the patient's cooperation (compliance), and complicates monitoring of the administered doses. Consequently, an object of the present invention is to provide a pharmaceutical agent which makes it possible to administer magnesium and iron compounds simultaneously without reducing the iron resorption. This will eliminate the disadvantages inherent in the conventional techniques described above.

SUMMARY OF THE INVENTION

The object of the present invention is attained by orally administering the pharmaceutical agent (drug) described below. The pharmaceutical agent contains a combination of one or more pharmaceutically compatible iron compounds, one or more pharmaceutically compatible magnesium compounds, and if the magnesium compounds do not contain sufficient chlorine atoms to saturate the available magnesium valences, the pharmaceutical agent further contains one or more pharmaceutically compatible compounds able to produce chlorine ions in aqueous media. The pharmaceutical agent is manufactured with standard pharmaceutical solvents and/or thinners, and/or auxiliary matter.

BRIEF DESCRIPTION OF THE DRAWINGS

FIG. 1 shows a graph of the weight development of female Sprague-Dawley rats which were fed magnesium and iron deficient diets, as compared to rats which were fed a normal control diet.

FIG. 2 shows a graph of the iron and magnesium plasma content of Sprague-Dawley rats which had been administered different combinations of iron and magnesium salts.

DETAILED DESCRIPTION OF THE INVENTION

The present invention is based on the unexpected observation that simultaneous administration of pharmaceutical magnesium and iron compounds is possible without reducing the bioavailability of iron. The unexpected result is possible when a compound producing chlorine ions in aqueous media, together with magnesium and iron compounds, is administered in such a quantity that the exogenic chlorine ions released in the gastric fluid are at least equivalent to the available magnesium valences of the employed magnesium compounds. In the event of subacidification of the gastric fluid, it is advisable to add even larger quantities of the compound yielding chlorine ions in order to produce a physiological chlorine ion concentration as high as possible.

In other words, it is essential to the invention that chlorine ions are made available in the stomach in a quantity sufficient enough to saturate the magnesium valences. Such chlorine ions must be made available during simultaneous administration of a magnesium compound which does not contain any chlorine atoms for saturation of the magnesium valences, such as magnesium oxide, magnesium hydroxide, magnesium aspartate, magnesium glutamate, etc. When subacidification of the gastric fluid occurs, it is advisable to have ready a quantity of chlorine ions exceeding the quantity necessary to saturate the magnesium valences. If these conditions are met, the administered iron compound is then unexpectedly resorbed to the same extent, as in the case when no magnesium compound is administered simultaneously.

The same conditions apply if the drug described in the invention contains one or more calcium compounds, such as calcium salts. Such calcium salts include, for instance, calcium chloride, calcium gluconate, calcium aspartate, etc. These calcium salts are commonly used for elimination of the familiar calcium deficiency conditions. This means that when a chlorine-free calcium compound is employed in the drug described in the invention, as many chlorine ions must be made available by the compound providing the chlorine ions as are minimally equivalent to both calcium valences, i.e., per one calcium ion, two chlorine ions.

The compounds providing the chlorine ions, if necessary, employed in the drug described in the present invention, preferably consist of inorganic chlorides, particularly magnesium chloride, calcium chloride, iron (II) chloride, iron (III) chloride or potassium chloride or hydrochloric acid.

At normal pH concentrations of gastric fluid, the administration of one or more compounds providing chlorine ions may be omitted, if a magnesium compound and/or calcium compound is employed in which the magnesium valences or calcium valences are already saturated by the chlorine atoms This is the case with compounds such as magnesium chloride and calcium chloride.

Particularly preferred magnesium compounds for the present invention are magnesium aminodicarbonic acid chloride, magnesium aspartate chloride and magnesium glutamate chloride, all of which have been previously employed in magnesium therapy and are by far, best resorbed. The magnesium aminodicarboxylic acid chloride and its use thereof in therapy is already known in the art (cf., for example, West German Patent Application DE-OS 3238118, which describes a new process for producing these compounds).

Suitable magnesium compounds, whose freely available magnesium valences are not saturated by chlorine atoms, include magnesium oxide, magnesium hydroxide, magnesium carbonate, magnesium aspartate, magnesium glutamate, magnesium hydrogen phosphate, magnesium glycerophosphate, magnesium trisilicate, magnesium hydroxide carbonate, magnesium acetate, magnesium citrate, magnesium gluconate, magnesium lactate, magnesium orotate or magnesium aminodicarboxylic acid fluoride, bromide and iodide, which are also known as pharmaceuticals and whose production is described in the said West German DE OS 3238118. When these magnesium compounds whose freely available magnesium valences are not saturated by chlorine atoms are used in the present invention, compounds naturally providing chlorine ions should be included in the preparation.

Suitable iron compounds for the present invention preferably include salts of iron (II) and iron (III), especially the chloride salts. Furthermore, the ion sulfates and the iron gluconates are also suitable.

The pharmaceutical agents of the present invention may be produced by the conventional procedure of mixing the components together using well-known conventional solvents, thinners and/or carriers. The mixtures can then be prepared for dispensation in the usual forms, such as pills, capsules, granulates or solutions.

The daily administered dose of the pharmaceutical agent of the present invention should be between about 20 and about 240 mg magnesium, about 5 to about 100 mg iron, and about 500 to about 1,000 mg calcium.

EXAMPLE 1

Iron Resorption in Rats

Twenty-four female Sprague-Dawley rats with an initial weight of about 130 g were randomly split into four groups (n=6). During a period of 20 days, the animals received various diets. Group I served as a control group and received a deficient diet in powdery form, enriched with admixtures of 500 ppm magnesium aspartate hydrochloride and of 200 ppm ferrous gluconate. Groups II, III and IV received the deficient diet with no magnesium and no iron admixed. (Determined concentrations of the deficient diet: Mg: 87 ppm; Fe: 5.3 ppm). FIG. 1 shows the weight development of the control rats as compared to the rats on the deficient diet over the 20-day period. On the morning of the twenty-first day, the animals were taken off their food. After 24 hours, the animals were administered the following solutions with a pharyngeal tube:

| Group I: | 2 ml H$_2$O |
| Group II: | 2 ml Fe gluconate (=8.65 mg Fe) |
| Group III: | 1 ml Mg aspartate (=37.45 mg Mg) |
| | 1 ml Fe gluconate (=8.65 mg Fe) |
| Group IV: | 1 ml Mg aspartate HCl (=37.5 mg Mg) |
| | 1 ml Fe gluconate (=8.65 mg Fe) |

One animal from Group IV died shortly after pharyngeal administration.

After three hours, blood sampling was performed by puncturing the aorta abdominalis. In the plasma, the magnesium and iron concentrations were determined with atomic absorption spectrometry (AAS). The AAS results are set forth below in Table 1.

TABLE 1

| Group I | 3.325 ppm ± 0.65 (0.059 mmole/l) | 15.12 ppm ± 1.17 (n = 6) (0.62 mmole/l) |
|---|---|---|
| Group II | 3.6 ppm ± 0.69 (0.065 mmole/l) | 6.8 ppm ± 2.07 (n = 6) (0.25 mmole/l) |
| Group III | 2.78 ppm ± 0.5 (0.05 mmole/l) | 20.9 ppm ± 6.4 (n = 6) (0.86 mmole/l) |
| Group IV | 3.15 ppm ± 0.63 (0.056 mmole/l) | 27.33 ppm ± 5.9 (n = 5) (1.12 mmole/l) |

The group differences were determined through variance analysis and controlled by a multiple range test (Duncan) at the 95% level. Significant differences were noted with the iron concentration between Group II and III ($p<0.05$), i.e., the magnesium aspartate reduces the iron resorption, whereas magnesium aspartate hydrochloride shows no significant influence.

FIG. 2 compares the iron and magnesium plasma content of the rats of Groups I through IV.

While the invention has been disclosed by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

We claim:

1. An orally administered pharmaceutical drug useful for iron and magnesium substitutive therapy, consisting essentially of a combination of a therapeutically effective amount of one or more pharmaceutically and physiologically compatible iron compounds which do not interfere with enteral magnesium absorption, a therapeutically effective amount of magnesium-L-aspartate hydrochloride matter and sufficient chlorine atoms dissociable in aqueous media to saturate the available magnesium valances, said chlorine atoms available from chloride salts of aid magnesium compounds or from one or more pharmaceutically and physiologically compatible compounds providing chlorine ions in aqueous media.

2. The drug of claim 1 further consisting essentially of a therapeutically effective amount of one or more pharmaceutically and physiologically compatible calcium compounds, wherein the compounds providing the chlorine atoms are present in such an amount that the chlorine ions in the gastric fluid, after said drug is administered to a patient, are made available in a quantity at least equivalent to the valences of magnesium compounds and/or calcium compounds not saturated by chlorine atoms.

3. The drug of claim 1, wherein the compounds providing chlorine atoms are inorganic chlorides.

4. The drug of claim 3, wherein said inorganic chlorides are selected from the group consisting of magnesium chloride, calcium chloride, iron (II) chloride, iron (III) chloride, potassium chloride and chlorine hydrogen acid.

5. The drug of claim 1, wherein said one or more magnesium compounds contain inorganic chlorine.

6. The drug of claim 1, wherein said one or more iron compounds comprise salts of iron (II) and/or iron (III).

7. The drug of claim 6, wherein said salts of iron (II) are selected from the group consisting of chlorine, and gluconate.

8. The drug of claim 1, wherein said drug is manufactured in the form of capsules, pills, dragees, granulates or solutions.

9. The drug of claim 1, further consisting essentially of one or more pharmaceutically compatible calcium compounds.

10. The drug of claim 9, wherein the compounds providing the chlorine atoms are present in such an amount that the chlorine ions in the gastric fluid, after said drug is administered to a patient, are made available in a quantity at least equivalent to the valences of magnesium compounds and/or calcium compounds not saturated by chlorine atoms.

11. The drug of claim 9, wherein the compounds providing chlorine atoms are inorganic chlorides.

12. The drug of claim 11, wherein said inorganic chlorides are selected from the group consisting of magnesium chloride, calcium chloride, iron (II) chloride, iron (III) chloride, potassium chloride and chlorine hydrogen acid.

13. The drug of claim 9, wherein said one or more magnesium compounds contain inorganic chlorine.

14. The drug of claim 9, wherein said one or more iron compounds comprise salts of iron (II) and/or iron (III).

15. The drug of claim 14, wherein said salts of iron (II) are selected from the group consisting of chlorine, and gluconate.

16. The drug of claim 9, wherein said one or more calcium compounds comprise salts of calcium.

17. The drug of claim 16, wherein said salts of calcium are selected from the group consisting of calcium chloride, calcium aspartate hydrochloride and calcium glutamate hydrochloride.

18. The drug of claim 9, wherein said drug is manufactured in the form of capsules, pills, dragees, granulates or solutions.

* * * * *